United States Patent
Khalaj et al.

(10) Patent No.: US 9,764,116 B2
(45) Date of Patent: Sep. 19, 2017

(54) CATHETER INSERTION SITE PLUG

(71) Applicant: AVENT, INC., Alpharetta, GA (US)

(72) Inventors: Steve S. Khalaj, Laguna Hills, CA (US); Siddharth Desai, Ladera Ranch, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 14/143,351

(22) Filed: Dec. 30, 2013

(65) Prior Publication Data

US 2015/0182728 A1    Jul. 2, 2015

(51) Int. Cl.
*A61M 25/02* (2006.01)
*A61M 39/02* (2006.01)
*A61M 25/00* (2006.01)

(52) U.S. Cl.
CPC ........ *A61M 25/02* (2013.01); *A61M 39/0247* (2013.01); *A61M 2025/0018* (2013.01); *A61M 2025/028* (2013.01); *A61M 2039/0261* (2013.01); *A61M 2039/0273* (2013.01)

(58) Field of Classification Search
CPC ............ A61M 25/02; A61M 2025/024; A61M 2025/0246; A61M 2025/0253; A61M 2025/0266; A61M 2025/028
USPC .......................................... 604/174, 175, 180
See application file for complete search history.

(56) References Cited

U.S. PATENT DOCUMENTS

| | | | |
|---|---|---|---|
| 3,581,732 A | 6/1971 | Ruiz | |
| 4,659,329 A | 4/1987 | Annis | |
| 4,755,173 A * | 7/1988 | Konopka | A61M 25/0606 128/DIG. 26 |
| 4,898,587 A * | 2/1990 | Mera | A61M 25/02 128/DIG. 26 |
| 4,959,055 A * | 9/1990 | Hillyer | 604/179 |
| 4,973,314 A | 11/1990 | Garrett | |

(Continued)

FOREIGN PATENT DOCUMENTS

| | | |
|---|---|---|
| GB | 2 105 197 A | 3/1983 |
| WO | WO 03/068304 A1 | 8/2003 |

(Continued)

OTHER PUBLICATIONS

PCT Search Report, Mar. 6, 2015.

*Primary Examiner* — Bhisma Mehta
*Assistant Examiner* — Nilay Shah
(74) *Attorney, Agent, or Firm* — Dority & Manning, P.A.

(57) ABSTRACT

The present invention provides a catheter site insertion plug composed of a body that includes an upper surface, a lower surface and a protruding portion extending from the lower surface. The protruding portion of the body forms a frustum having a terminus and defines a passageway extending from an opening at the upper surface to an exit orifice at the terminus of the frustum. The passageway is configured to receive a catheter therethrough. The lower surface may include a second protruding portion in the form of an annular ring around the first protruding portion. The first protruding portion may include an end section that extends radially outward to provide an inflection point generally adjacent the terminus of the frustum. The end section may extend outward to provide at least one radial edge. The present invention also provides a catheter system composed of a flexible catheter and catheter site insertion plug.

9 Claims, 6 Drawing Sheets

(56) References Cited

U.S. PATENT DOCUMENTS

| | | | |
|---|---|---|---|
| 5,405,388 A | 4/1995 | Fox | |
| 5,690,616 A | 11/1997 | Mogg | |
| 5,713,858 A | 2/1998 | Heruth et al. | |
| 5,873,864 A * | 2/1999 | Luther | A61M 25/0068 604/175 |
| 5,990,382 A | 11/1999 | Fox | |
| 6,685,674 B2 * | 2/2004 | Douglas | A61M 5/158 604/167.05 |
| 7,524,300 B2 * | 4/2009 | Patton | A61M 39/0247 604/180 |
| 8,152,792 B1 | 4/2012 | Kornel | |
| 8,366,683 B2 * | 2/2013 | Patton | 604/244 |
| 8,684,974 B2 * | 4/2014 | Richard | 604/167.01 |
| 2003/0093075 A1 | 5/2003 | Levinson | |
| 2005/0113761 A1 * | 5/2005 | Faust et al. | 604/180 |
| 2005/0119637 A1 | 6/2005 | Lundgren et al. | |
| 2006/0276837 A1 | 12/2006 | Bergin et al. | |
| 2008/0021375 A1 * | 1/2008 | Burns | A61M 39/0247 604/27 |
| 2008/0243085 A1 * | 10/2008 | DeStefano | 604/180 |
| 2008/0312598 A1 * | 12/2008 | Douglas et al. | 604/167.01 |
| 2009/0192467 A1 * | 7/2009 | Hansen et al. | 604/174 |
| 2012/0245529 A1 * | 9/2012 | Hummen et al. | 604/175 |
| 2013/0289338 A1 | 10/2013 | Couch et al. | |

FOREIGN PATENT DOCUMENTS

| | | |
|---|---|---|
| WO | WO 2008/119041 A1 | 10/2008 |
| WO | WO 2012/020246 A1 | 2/2012 |

* cited by examiner

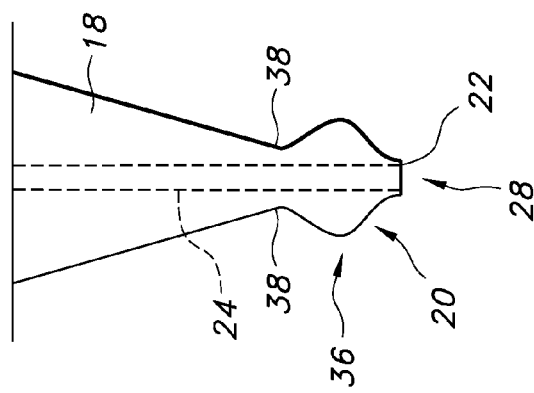
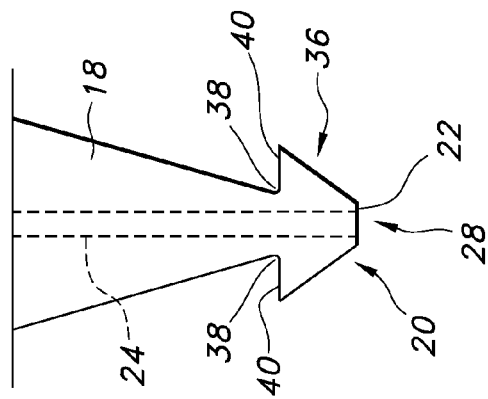
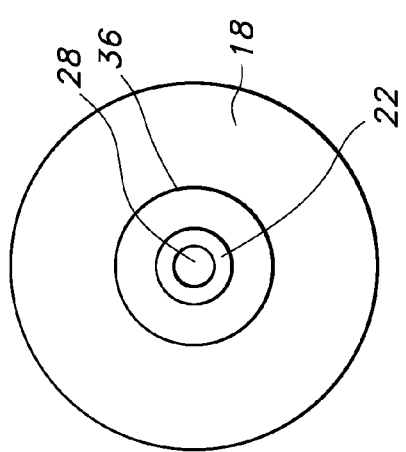
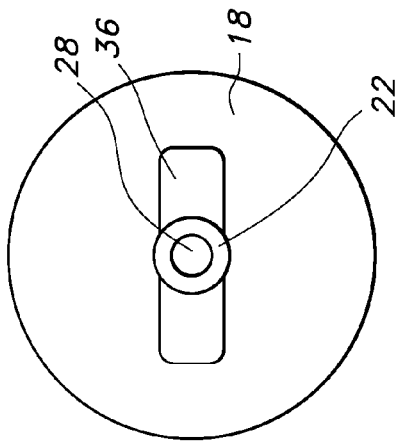
FIG. 2A
FIG. 2B
FIG. 2C
FIG. 2D

CATHETER INSERTION SITE PLUG

FIELD OF THE INVENTION

The present invention relates generally to infusion catheters. More particularly, the present invention relates to an accessory used with an infusion catheter.

BACKGROUND OF THE INVENTION

Infusion catheters for delivery of fluid medication into anatomical systems, such as the human body, are known in the art. Such catheters generally include a flexible hollow tube inserted into some region of the anatomy. The tube typically contains one or more axial lumens within which the fluid may flow. The proximal end of the catheter tube is connected to a fluid source from which fluid is introduced into the catheter tube. The fluid flows within one of the lumens under pressure supplied at the proximal end of the tube. For each lumen, there are commonly provided one or more exit holes along an infusion section near the distal end of the tube, for fluid to exit the tube.

Such infusion catheters are typically inserted into a tunnel or opening into the skin—sometimes referred to as an insertion site or skin puncture site. The catheter extends into the anatomy to a site where it is desirable to deliver fluid medication. After a catheter is inserted, it is important to maintain the catheter in position to properly deliver the fluid medication. Infusion catheters are typically small-diameter flexible tubes that can be easily pulled out or disturbed if they are not well secured. In the past, catheters have been sutured to the skin or secured in place by various techniques utilizing adhesive tape. These techniques provide inconsistent results and can result in movement of the catheter, leakage of fluid medication at the point of insertion, kinking of the catheter that may reduce or obstruct fluid flow.

In addition, infusion catheters may leak at the location where the catheter is inserted into the skin. For example, the diameter of the skin puncture site may be slightly greater than the diameter of the catheter such that fluid delivered through the catheter may travel along the catheter and out of the opening. Typically, the skin puncture site is sealed using medical adhesive. However, the medical adhesive may not seal completely and may complicate removal of the catheter.

Accordingly, there is a need for a practical and cost-effective device for securing the catheter in position and for minimizing or preventing leakage of fluid medication through the skin puncture site. There is also a need for a practical and cost-effective device for securing a catheter and for minimizing or preventing leakage of fluid medication that does not require a separate step of applying an adhesive to secure the skin at the skin puncture site. Meeting these needs is important because catheters that are not secured may crimp or kink and leakage of fluid medication may increase the risk of infection. Crimping or kinking a catheter may require a doctor to remove and replace the damaged catheter incurring additional expense of time and medical supplies and exposing a patient to increased risk of infection or trauma.

SUMMARY OF THE INVENTION

Generally stated, the present invention provides a catheter site insertion plug for reducing or preventing leakage at a skin puncture site. The catheter site insertion plug is composed of a body that includes an upper surface, a lower body-contacting surface and a protruding portion extending from the lower surface. The protruding portion of the body forms a frustum having a terminus and defines a passageway extending from an opening at the upper surface to an exit orifice at the terminus of the frustum. The passageway is configured to receive a catheter therethrough.

According to an aspect of the invention, the portion of the body defining the passageway may define a beveled or curved opening to the passageway at the upper surface to facilitate insertion of a catheter into the passageway. The lower surface of the body may include a second protruding portion in the form of an annular ring around the first protruding portion. The upper surface of the body may further include one or more notches for receiving and securing a catheter.

In another aspect of the invention, the first protruding portion may include an end section that extends radially outward to provide an inflection point generally adjacent the terminus of the frustum. The end section may extend radially outward to provide at least one radial edge.

The catheter site insertion plug may further include a base. For example, the base may be a foam element or composite material that helps stabilize and/or cushion the catheter site insertion plug when it is positioned on the skin of a patient. The base may include a skin contacting portion that may further include a skin-compatible adhesive.

The present invention also provides a catheter system composed of a flexible catheter such as, for example, an infusion catheter, and a catheter site insertion plug as described above. Generally speaking, the flexible catheter is sized to substantially occupy the passageway extending through the protruding portion of the catheter site insertion plug.

A better understanding of the above-described catheter site insertion plug and many other features and advantages of the catheter system incorporating the catheter site insertion plug may be obtained from a consideration of the detailed description of the invention below, particularly if such consideration is made in conjunction with the appended drawings.

BRIEF DESCRIPTION OF THE DRAWINGS

FIG. 2A shows a side view of a detail of a portion of an exemplary catheter site insertion plug.

FIG. 2B shows a side view of a detail of a portion of an exemplary catheter site insertion plug.

FIG. 2C shows a bottom view of a detail of a portion of an exemplary catheter site insertion plug.

FIG. 2D shows a bottom view of a detail of a portion of an exemplary catheter site insertion plug.

DEFINITIONS

Figure 1A:
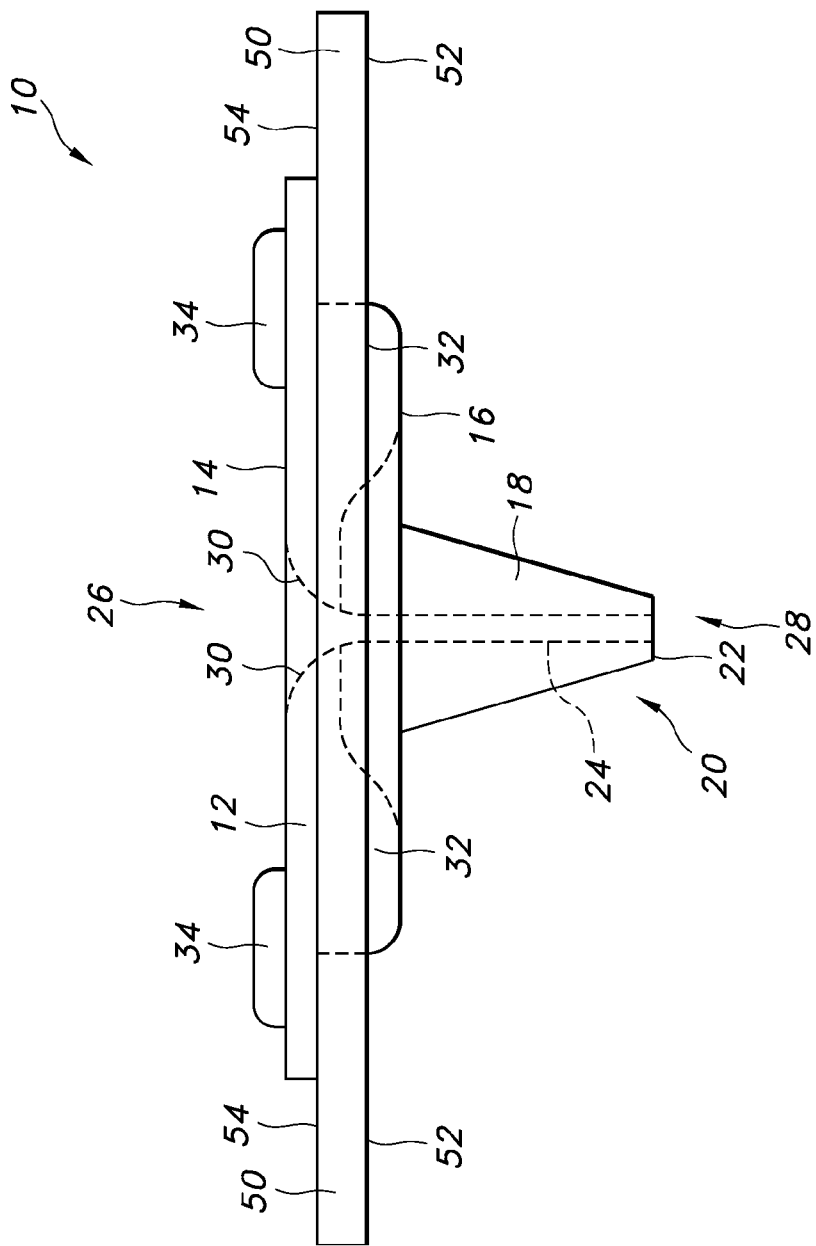
FIG. 1A shows a side view of an exemplary catheter site insertion plug including a base.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered and, more desirably, more than 90% covered.

As used herein, the terms "position," and/or "positioned," refers to the spatial property possessed by an arrangement or location of things in a particular relationship, alignment, formation or conformation.

As used herein, the terms "orientation" or "position" used interchangeably herein refer to the spatial property of a place where something is situated or a way in which something is situated; for example, "the position of the hands on the clock."

As used herein, the term "about" adjacent to a stated number refers to an amount that is plus or minus ten (10) percent of the stated number.

DETAILED DESCRIPTION OF THE INVENTION

The invention(s) disclosed herein relate generally to a catheter site insertion plug. More particularly, the invention(s) disclosed herein relate to a catheter site insertion plug having a protruding portion that is positioned in a skin puncture site to reduce or prevent leakage out of the skin puncture site. The catheter site insertion plug also has a passageway that is configured to receive a catheter that is sized to substantially occupy the passageway.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Turning now to the drawings, the invention is generally illustrated in side view at FIG. 1A which shows an exemplary catheter site insertion plug 10 that includes a body 12 having an upper surface 14 and a lower, body-contacting surface 16. The body 12 also defines a protruding portion 18 extending from the lower surface 16. The protruding portion 18 may desirably be conical and have a generally circular, oval or ellipsoidal cross-section. It is contemplated that the protruding portion may be pyramidal or may be configured to have any generally taping geometric configuration.

The protruding portion 18 of the body 12 forms a frustum 20. That is, the frustum 20 is the part of the protruding body formed by cutting off the tip of cone, pyramid or similar shape. The frustum 20 has a terminus 22 that is illustrated as generally parallel with the upper surface 14 and/or lower surface 16 of the body 12. It is contemplates that the terminus 22 may define an angle with respect to the upper surface 14 and/or lower surface 16 of the body 12. The body 12 defines a passageway 24 extending from an opening 26 at the upper surface 14 to an exit orifice 28 at the terminus 22 of the frustum 20. The passageway 24 is configured to receive a catheter therethrough (See FIG. 5).

According to an aspect of the invention, the portion of the body defining the passageway may define a beveled or curved opening 30 to the passageway 24 at the upper surface 14 to facilitate insertion of a catheter into the passageway.

Figure 1B:
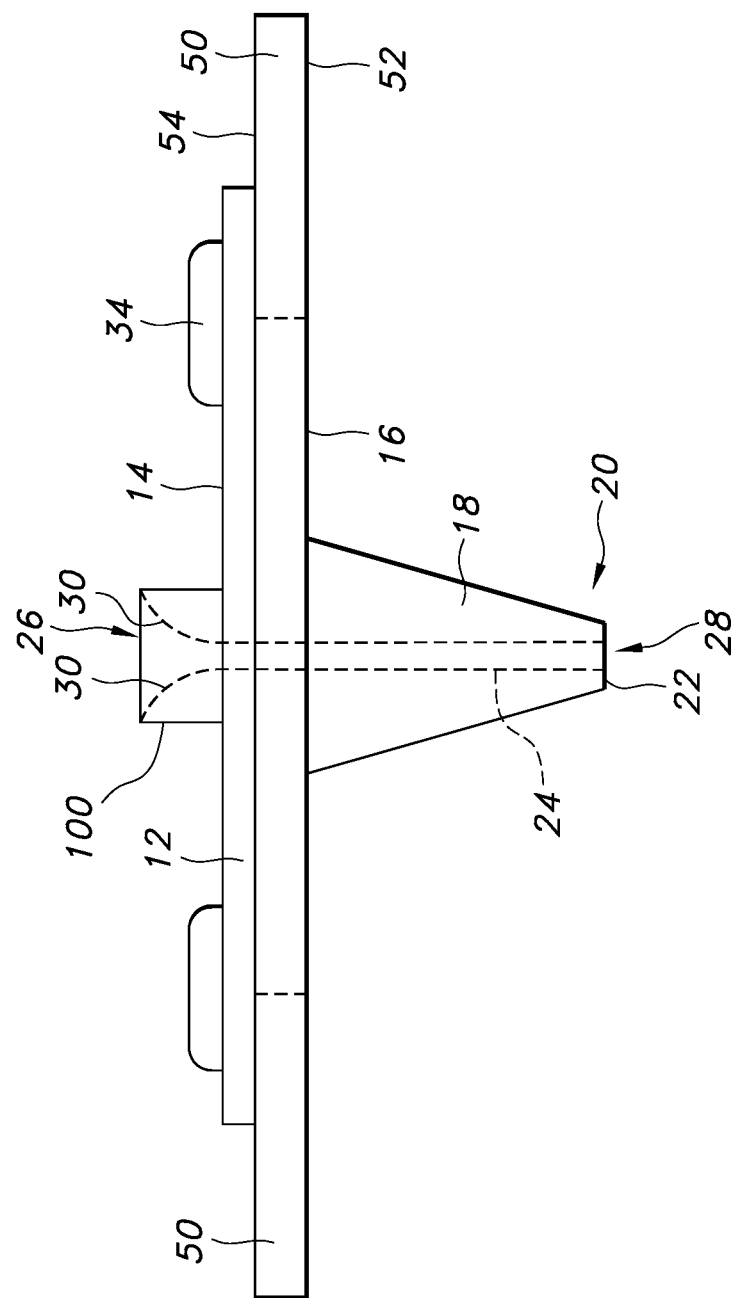
FIG. 1B shows a side view of an exemplary catheter site insertion plug including a base.
Figure 3:
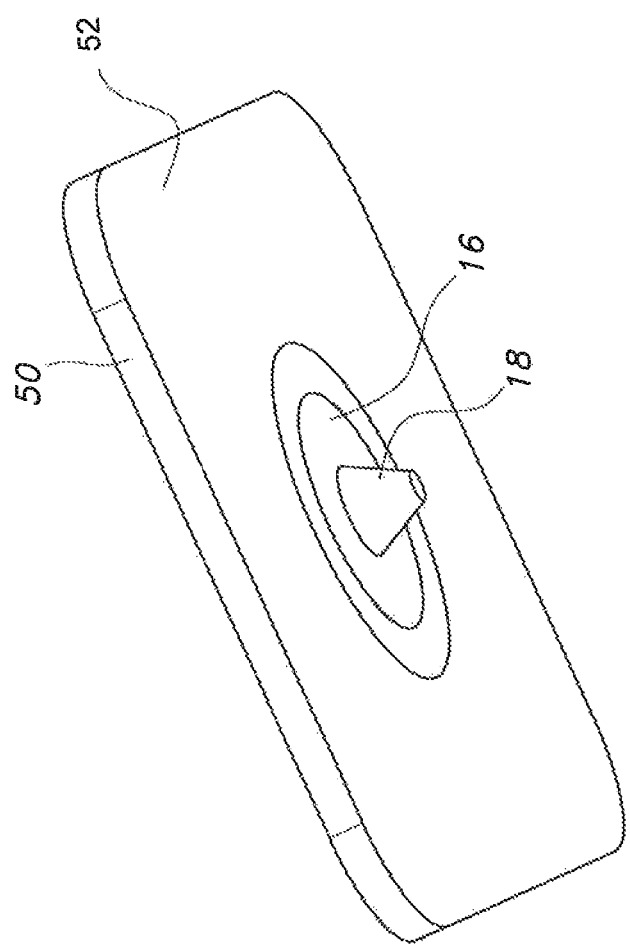
FIG. 3 shows a bottom perspective view of an exemplary catheter site insertion plug.

The lower surface 16 of the body may include an optional second protruding portion 32 in the form of an annular ring around the first protruding portion 18. Generally speaking, the second protruding portion should push or direct the skin against the first protruding portion to provide a better seal. The force that pushes or directs the skin is provided by a dressing, tape, or pressure from an adhesive base, or the like. It is contemplated that the second protruding portion may have other geometric configurations such as ripples or bumps that perform the same function. FIG. 1B is an illustration showing a side view of an exemplary catheter site insertion plug without the optional second protruding portion. In addition, FIG. 1B illustrates a raised portion 100 of the body 12 defining an opening 26 to the passageway 24.

The upper surface 14 of the body may further include one or more notches or features 34 for receiving and securing a catheter. For example, the notches 34 may frictionally engage a catheter.

Referring now to FIG. 2A of the drawings there is illustrated in side view another aspect of the invention. The first protruding portion 18 may include an end section 36 that extends radially outward to provide an inflection point 38 generally adjacent the terminus 22 of the frustum 20. In other words, the end section may provide a bulge at the end of the protruding portion. The bulge helps anchor the catheter site insertion plug in the skin puncture site. Referring to FIG. 2B, there is illustrated in side view yet another aspect of the invention. The first protruding portion 18 may include an end section 36 that extends radially outward to provide an inflection point 38 generally adjacent the terminus 22 of the frustum 20. The inflection point 38 may be sufficiently acute that the end section provides at least one radial edge 40. In other words, the end section may provide a barb at the end of the protruding portion. Referring to FIG. 2C, there is a bottom view of the protruding portion showing the exit orifice 38 surrounded by the terminus 22 of the frustum, the end section 36 and the protruding portion 18. In this illustration, the end section 36 is illustrated as extending radially outward in a uniform manner. It is contemplated that the end section may extend radially outward in a non-uniform manner to have an oval, ellipsoidal or other cross-section. In this regard, FIG. 2D illustrates a bottom view of the protruding portion showing the exit orifice 38 surrounded by the terminus 22 of the frustum, the end section 36 and the protruding portion 18. In this illustration, the end section 36 extends radially outward in a non-uniform manner to form lobes.

According to an aspect of the present invention, the catheter site insertion plug body may be formed as a unitary or monolithic element. That is, the body may be one piece formed of the same material. Alternatively, an upper portion of the body defining the upper surface 14 and/or the lower surface 16 may be formed of a rigid material and a protruding portion 18 may be formed of another material. Desirably, the protruding portion 18 may be formed of an elastomeric material such as, for example, a medical grade elastomeric silicone. The elastomeric silicone desirably has a Shore Hardness (durometer hardness) of about 10 A to about 80 A (as initially reported by the manufacturer) and has a generally similar Shore Hardness (durometer hardness) after processing into the catheter site insertion plug. More desirably, the elastomeric silicone has a Shore Hardness (durometer hardness) of about 15 A to about 50 A. For example, the elastomeric silicone has a Shore Hardness (durometer hardness) of about 25 A to about 50 A. As another example, the elastomeric silicone may have a Shore Hardness (durometer hardness) of about 40 A.

Referring to 3 of the drawings, there is shown in bottom perspective view an exemplary catheter site insertion plug 10 including an optional base which is also referred to as an anchor pad 50. The anchor pad 50 may be any suitable substantially flat piece of material such as, for example, a foam element or composite material that helps stabilize and/or cushion the catheter site insertion plug when it is positioned on the skin of a patient. The proximal, or lower, side 52 of the pad faces toward the skin of the patient, and is desirably covered with an adhesive surface suitable for attaching the anchor pad 50 to the skin of the patient. The upper side 54 of the anchor pad faces away from the skin of the patient and supports the catheter site insertion plug. The anchor pad 50 desirably is composed of a laminate structure with an upper foam layer (e.g., closed-cell polyethylene foam) and a lower adhesive layer. The lower adhesive layer constitutes the lower surface of the anchor pad. The lower surface desirably is a medical-grade adhesive. Such foams with an adhesive layer are available commercially from a variety of manufacturers.

A surface of the upper foam layer may constitute the upper surface of the anchor pad. The upper surface can be roughened by chemical priming or corona-treating the foam with a low electric charge. The roughened or porous upper surface can improve the quality of the adhesive joint (which is described below) between the base of the catheter site insertion plug and the anchor pad. In alternative examples, the flexible anchor pad can include a medical-grade adhesive lower layer, an inner foam layer and an upper paper or other woven or nonwoven cloth layer.

The lower surface of the anchor pad may include a region of hydro-colloid adhesive disposed centrally on the anchor pad in the region corresponding to the skin puncture site. This hydro-colloid region provides an adhesive which is less irritating to sensitive skin on the portion of the anchor pad which is closest to the catheter insertion site.

A removable paper or plastic release liner desirably covers the adhesive lower surface before use. The release liner desirably resists tearing and desirably is divided into a plurality of pieces to ease attachment of the anchor pad to a patient's skin. For example, the release liner may be split along a centerline of the anchor pad in order to expose only half of the adhesive lower surface at one time.

The length of each release liner piece may extend beyond a centerline of the anchor pad and may be folded over, or back onto the release liner. This folded over portion defines a pull-tab to facilitate removal of the release liner from the adhesive lower surface. A healthcare worker uses the pull-tab by grasping and pulling on it so that the release liner is separated from the lower surface. The pull-tab eliminates the need to pick at a corner edge or other segment of the release liner in order to separate the release liner from the adhesive layer. The pull-tab can be designed in a variety of configurations. For example, the pull-tab need not be located along a centerline of the anchor pad; rather, the pull-tab can be located along any line of the anchor pad in order to ease the application of the anchor pad onto the patient's skin at a specific site.

Figure 4:
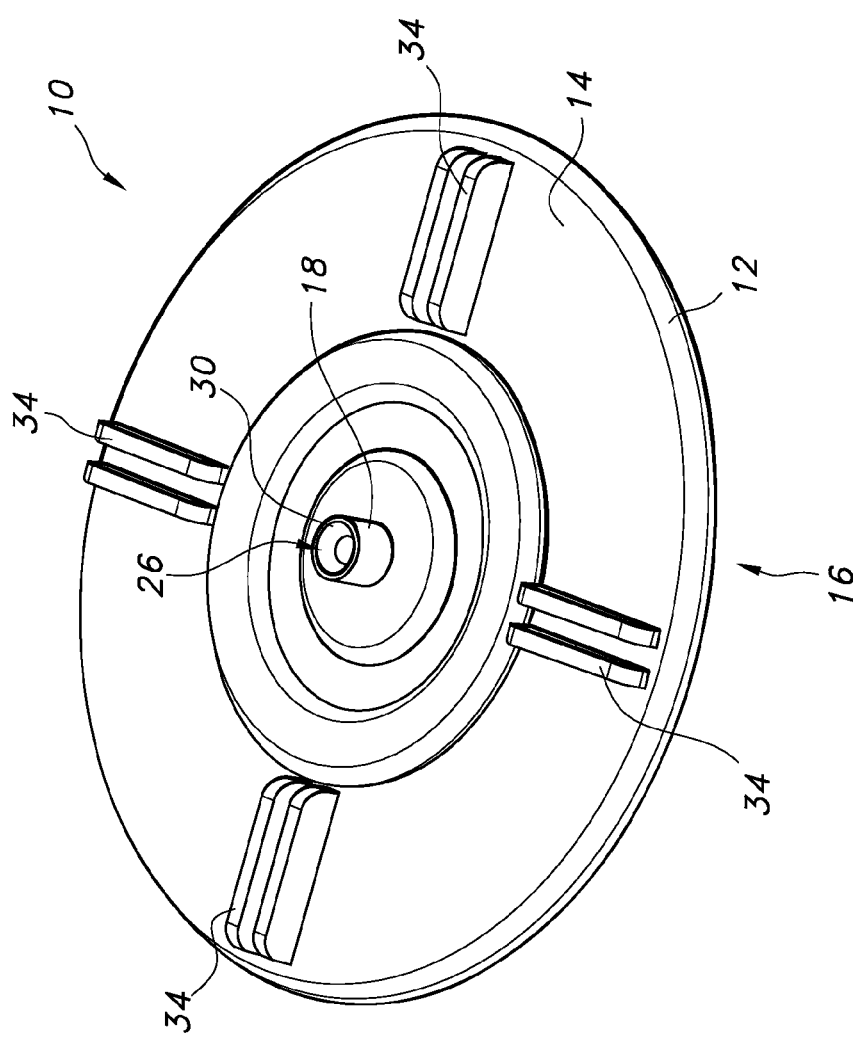
FIG. 4 shows a top perspective view of an exemplary catheter site insertion plug.

Referring to FIG. 4 of the drawings, there is illustrated a top perspective view of an exemplary catheter site insertion plug 10 (without an optional base or anchor pad) showing an upper surface 14 of the body 12 incorporating include one or more notches or features 34 for receiving and securing a catheter. For example, the notches 34 may frictionally engage a catheter.

Figure 5:
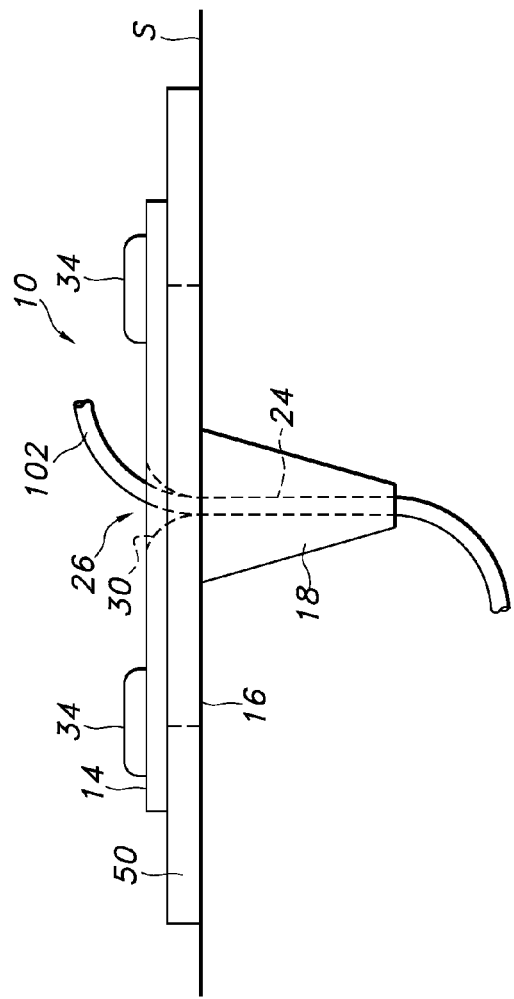
FIG. 5 shows a side, partial cross-section view of an exemplary catheter system composed of a catheter and an exemplary catheter site insertion plug.
Figure 6:
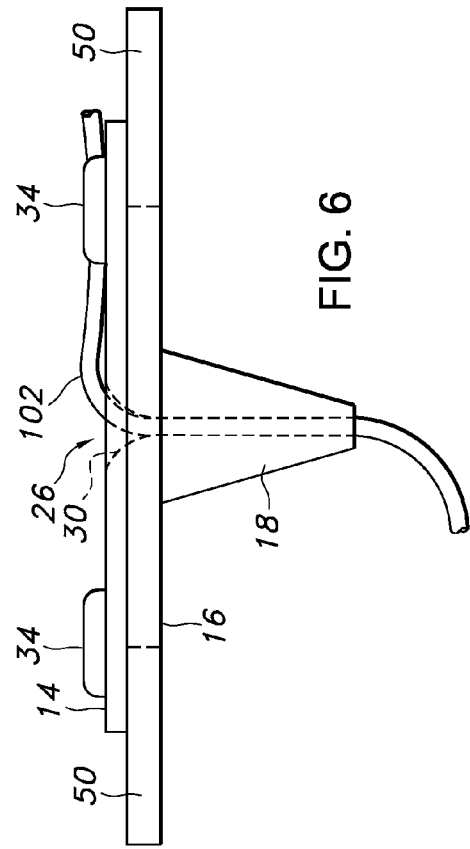
FIG. 6 shows a side, partial cross-section view of an exemplary catheter system composed of a catheter and an exemplary catheter site insertion plug.

Referring now to FIGS. 5 and 6 of the drawings, the present invention encompasses a catheter system composed of a flexible catheter 102 and a catheter site insertion plug 10 as generally described above. Generally speaking, the flexible catheter 102 is sized to substantially occupy the passageway 24 extending through the protruding portion 18 of the catheter site insertion plug 10. For example, the flexible catheter 102 may occupy 70% of the cross-sectional area of at least a portion or region of the passageway 24. More desirably, the flexible catheter 102 may occupy 90% or more of the cross-sectional area of at least a portion or region of the passageway 24. More desirably, the flexible catheter 102 may fully occupy the cross-sectional area of at least a portion or region of the passageway 24. This relationship between the flexible catheter 102 and the cross-sectional area of at least a portion or region of the passageway is desirable to prevent fluid medication from flowing back up through the passageway. As illustrated in FIG. 5, the catheter site insertion plug 10 rests on the surface of the skin "S" of a patient. The protruding portion 18 rests in a skin puncture site through the skin to fill the volume of the opening to prevent fluid medication from leaking.

In addition, the catheter system is advantageous at least because it allows for ease of threading the catheter 102 through the passageway 24 of the catheter site insertion plug 10 because the opening 26 has curved or beveled edges 30. Moreover, the catheter site insertion plug allows the catheter 102 to be secured in the notch or feature 34 to frictionally engage the catheter as shown in FIG. 6. Exemplary catheters include infusion catheters such as those described at, for example, by U.S. Pat. No. 6,350,253; U.S. Pat. No. 7,004,923; U.S. Pat. No. 7,438,711; U.S. Pat. No. 7,452,353; U.S. Pat. No. 7,527,609; U.S. Pat. No. 7,547,302; U.S. Pat. No. 7,780,638; U.S. Pat. No. 8,328,771; and U.S. Pat. No. 8,343,135; the contents of each are incorporated herein by reference.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. A catheter site insertion plug comprising:
  a base that includes:
    a top surface and a bottom surface, and
    a body integrated with the base, the body having an upper surface, a lower-most surface, and a first protruding portion extending from the lower-most surface, the first protruding portion comprising a flexible frustum defining a surface that tapers from a first end to a second end, the first end of the tapered frustum being mounted to the lower-most surface such that the frustum is positioned completely outside the body of the insertion plug, the second end of the tapered frustum defining a distal-most end of the insertion plug, the first protruding portion further comprising an end section that extends radially outward to provide an inflection point generally adjacent to the distal-most end of the insertion plug, the body defining a passageway extending from an opening at the upper surface to an exit orifice at the distal-most end of the insertion plug, the passageway configured to receive a catheter therethrough.

2. The catheter site insertion plug of claim 1, wherein the body defining the passageway defines a beveled or curved opening to the passageway at the upper surface to facilitate insertion of the catheter into the passageway.

3. The catheter site insertion plug of claim 1, wherein the body further includes a second protruding portion extending from the bottom surface of the base, the second protruding portion being in the form of an annular ring around the first protruding portion.

4. The catheter site insertion plug of claim 1, wherein the end section that extends radially outward provides at least one radial edge generally adjacent the distal-most end of the insertion plug.

5. The catheter site insertion plug of claim 1, wherein the upper surface further includes a notch for receiving and securing the catheter.

6. The catheter site insertion plug of claim 1, wherein the bottom surface of the base includes a skin contacting portion incorporating a skin-compatible adhesive.

7. A catheter system comprising:
a flexible catheter; and
a catheter site insertion plug comprising:
    a body that includes:
        an upper surface,
        a lower-most, body-contacting surface, and
        a first protruding portion extending from the lower-most surface, the first protruding portion comprising a flexible frustum defining a smooth, continuous surface that tapers from a first end to a second end, the first end of the tapered frustum being mounted to the lower-most surface, the second end defining a distal-most end of the insertion plug,
    wherein the flexible catheter is sized to substantially occupy a passageway extending through the first protruding portion of the catheter site insertion plug.

8. The catheter system of claim 7, wherein the body defining the passageway defines a beveled or curved opening to the passageway at the upper surface to facilitate insertion of the catheter into the passageway.

9. The catheter site insertion plug of claim 7, wherein the lower-most surface further includes a second protruding portion in the form of an annular ring around the first protruding portion.

* * * * *